United States Patent
Jung et al.

(10) Patent No.: US 12,427,063 B2
(45) Date of Patent: Sep. 30, 2025

(54) DYNAMIC LASER PULSE CONTROL

(71) Applicant: Alcon Inc., Fribourg (CH)

(72) Inventors: David Jung, Tustin, CA (US); Francisco Javier Ochoa, La Mirada, CA (US); Daniel Castro, Lake Forest, CA (US); Corey Stewart, Irvine, CA (US); Keith Watanabe, Irvine, CA (US)

(73) Assignee: Alcon Inc., Fribourg (CH)

( * ) Notice: Subject to any disclaimer, the term of this patent is extended or adjusted under 35 U.S.C. 154(b) by 475 days.

(21) Appl. No.: 18/046,006

(22) Filed: Oct. 12, 2022

(65) Prior Publication Data
US 2023/0116921 A1    Apr. 20, 2023

Related U.S. Application Data

(60) Provisional application No. 63/256,071, filed on Oct. 15, 2021.

(51) Int. Cl.
*A61F 9/008* (2006.01)
*G02B 26/02* (2006.01)
(Continued)

(52) U.S. Cl.
CPC ............ *A61F 9/008* (2013.01); *G02B 26/023* (2013.01); *G02B 26/0816* (2013.01);
(Continued)

(58) Field of Classification Search
CPC ... A61F 9/008; G02B 26/023; G02B 26/0816; A61B 2017/00154; A61B 2017/00973; A61B 2018/00702
See application file for complete search history.

(56) References Cited

U.S. PATENT DOCUMENTS

| 5,225,884 A | 7/1993 | Stark et al. |
| 6,055,259 A | 4/2000 | Frey et al. |

(Continued)

FOREIGN PATENT DOCUMENTS

| CN | 102749786 A | 10/2012 |
| DE | 3333575 C2 | 9/1992 |

(Continued)

OTHER PUBLICATIONS

Anonymous: "Kuhnke Laser Shutter DS200x8", KENDRIONS—Technical information, Feb. 21, 2017, XP002806981. Retrieved from the Internet: URL: https://www.kendrion.com/fileadmin/user_upload/Downloads/Brochures_and_Flyers/Electromagnets_Actuators/brochure-lasershutter-ds200x8-kendrion-kuhnke.pdf [retrieved on Jul. 1, 2022].

(Continued)

*Primary Examiner* — Scott M. Getzow
(74) *Attorney, Agent, or Firm* — Patterson + Sheridan, LLP

(57) ABSTRACT

Systems and methods are disclosed for dynamically controlling laser pulses being output from a laser system. An example surgical system comprises a laser, an optical switching device, an adjustable input device such as a foot pedal, and a laser pulse controller. An operator actuates the adjustable input device over an operating range to control dynamically the laser pulses being output from the laser system. In one mode, the adjustable input device may dynamically control output laser energy. In another mode, the adjustable input device may dynamically control selection of laser pulses to be output from the system.

14 Claims, 7 Drawing Sheets

(51) Int. Cl.
*G02B 26/08* (2006.01)
*A61B 17/00* (2006.01)
*A61B 18/00* (2006.01)

(52) U.S. Cl.
CPC ............ *A61B 2017/00154* (2013.01); *A61B 2017/00973* (2013.01); *A61B 2018/00702* (2013.01)

(56) References Cited

U.S. PATENT DOCUMENTS

| | | | |
|---|---|---|---|
| 6,067,311 A | 5/2000 | Morton et al. | |
| 6,080,148 A | 6/2000 | Damasco | |
| 6,156,030 A | 12/2000 | Neev | |
| 7,479,138 B2 | 1/2009 | Hindi et al. | |
| 7,630,418 B2 | 12/2009 | Franjic et al. | |
| 7,696,466 B2 | 4/2010 | Rizoiu et al. | |
| 8,025,659 B2 | 9/2011 | Bischoff et al. | |
| 8,029,501 B2 | 10/2011 | Miller | |
| 8,279,901 B2 | 10/2012 | Karavitis | |
| 8,506,559 B2 | 8/2013 | Raksi | |
| 8,518,030 B2 | 8/2013 | Holliday | |
| 8,652,122 B2 | 2/2014 | Bischoff et al. | |
| 8,920,407 B2 | 12/2014 | Raksi et al. | |
| 9,044,303 B2 | 6/2015 | Kurtz et al. | |
| 9,054,479 B2 | 6/2015 | Karavitis | |
| 9,660,412 B2 | 5/2017 | Vogler et al. | |
| 9,724,235 B2 | 8/2017 | Vogler et al. | |
| 9,755,393 B2 | 9/2017 | Vogler et al. | |
| 9,931,447 B2 | 4/2018 | Layser | |
| 10,512,586 B1 | 12/2019 | Lee | |
| 10,624,786 B2 | 4/2020 | Wysopal et al. | |
| 10,702,338 B2 | 7/2020 | Shazly et al. | |
| 10,881,551 B2 | 1/2021 | Kraemer et al. | |
| 10,925,769 B2 | 2/2021 | Kraemer | |
| 11,197,781 B2 | 12/2021 | Wittnebel | |
| 2001/0010003 A1 | 7/2001 | Lai | |
| 2005/0105568 A1* | 5/2005 | Smart | H01S 3/0057 372/13 |
| 2008/0121627 A1* | 5/2008 | Bruland | B23K 26/042 257/E23.15 |
| 2009/0213330 A1 | 8/2009 | Silverstein et al. | |
| 2013/0226157 A1 | 8/2013 | Huang | |
| 2014/0128856 A1* | 5/2014 | Wysopal | A61F 9/00825 606/5 |
| 2014/0276676 A1 | 9/2014 | Schuele et al. | |
| 2015/0034613 A1 | 2/2015 | Hosseini | |
| 2018/0360657 A1 | 12/2018 | Bor et al. | |
| 2019/0201238 A1 | 7/2019 | Bacher et al. | |
| 2021/0135424 A1 | 5/2021 | Bacher et al. | |
| 2021/0137739 A1 | 5/2021 | Kraemer | |
| 2022/0354575 A1* | 11/2022 | Jung | G02F 1/133638 |
| 2023/0113339 A1 | 4/2023 | Ovchinnikov | |
| 2023/0178953 A1 | 6/2023 | Karim et al. | |

FOREIGN PATENT DOCUMENTS

| | | |
|---|---|---|
| KR | 20130109664 A | 10/2013 |
| RU | 2349998 C2 | 3/2009 |
| WO | 2009108543 A2 | 9/2009 |

OTHER PUBLICATIONS

Peter Gregorčič, Matija Jezeršek, and Janez Možina, Optodynamic energy-conversion efficiency during an Er:YAG-laser-pulse delivery into a liquid through different fiber-tip geometries, Journal of Biomedical Optics 17(7), 075006 (Jul. 2012)).

Wikipedia. "Optical Chopper." Retrieved from https://en.wikipedia.org/w/index.php?title=Optical_chopper&oldid=943497792 on May 12, 2020.

Mielke, Michael, et al., "Pulse and amplifier dynamics in high energy fiber optic ultrashort pulse laser systems," Spie Smart Structures and Materials + Nondestructive Evaluation and Health Monitoring, vol. 7214, Feb. 12, 2009.

* cited by examiner

Sculpt Mode : All Pulses are Passed

Quad Mode (500 Hz) : One Pulse is Passed Per Pulse Picking Cycle

Quad Mode (250 Hz) : One Pulse is Passed Per Pulse Picking Cycle

Quad Mode (166 Hz) : One Pulse is Passed Per Pulse Picking Cycle

Quad Mode (125 Hz) : One Pulse is Passed Per Pulse Picking Cycle

Quad Mode (125 Hz) : 2 Pulses are Passed Per Pulse Picking Cycle

Quad Mode (125 Hz) : 3 Pulses are Passed Per Pulse Picking Cycle

Quad Mode (125 Hz) : 4 Pulses are Passed Per Pulse Picking Cycle

DYNAMIC LASER PULSE CONTROL

PRIORITY CLAIM

This application claims the benefit of priority of U.S. Provisional Patent Application Ser. No. 63/256,071 titled "DYNAMIC LASER PULSE CONTROL," filed on Oct. 15, 2021, whose inventors are David Jung, Francisco Javier Ochoa, Daniel Castro, Corey Stewart and Keith Watanabe, which is hereby incorporated by reference in its entirety as though fully and completely set forth herein.

TECHNICAL FIELD

The present disclosure is directed to systems and methods for dynamically controlling laser pulses being output from a laser system.

BACKGROUND

Lasers are used in many different medical procedures including a number of different ophthalmic procedures. For example, lasers may be used in cataract surgery, such as for fragmenting the cataractous lens. In some procedures, a laser is used for initial fragmentation of the lens, followed by phacoemulsification of the lens by an ultrasonic handpiece to complete the breakdown of the lens for removal. In other procedures, the laser may be used for complete fragmentation and/or phacoemulsification of the lens for removal, without the need for a separate application of ultrasonic energy. Lasers may also be used for other steps in cataract surgery, such as for making the corneal incision(s) and/or opening the capsule.

Lasers may also be used in vitreoretinal surgery. In some procedures, a laser may be used for vitrectomy, to sever or break the vitreous fibers for removal. The laser may be incorporated into a vitrectomy probe, and the energy from the laser may be applied to the vitreous fibers to sever or break the vitreous fibers for removal.

In other vitreoretinal applications, lasers may be used for photocoagulation of retinal tissue. Laser photocoagulation may be used to treat issues such as retinal tears and/or the effects of diabetic retinopathy.

U.S. Patent Application Publication No. 2018/0360657 discloses examples of an ophthalmic laser system. That application describes laser uses such as for forming surgical cuts or for photodisrupting ophthalmic tissue as well as for cataract surgery, such as laser-assisted cataract surgery (LACS). U.S. Patent Application Publication No. 2019/0201238 discloses other examples of an ophthalmic laser system. That application describes laser uses such as in a vitrectomy probe for severing or breaking vitreous fibers. U.S. Patent Application Publication No. 2018/0360657 and U.S. Patent Application Publication No. 2019/0201238 are expressly incorporated by reference herein in their entirety.

Some laser systems emit pulses, with the pulses having a desired duration and repetition rate. Operating a laser in pulses can achieve desirable power and energy characteristics for a particular application. In addition, while the energy of a beam emitted by a laser can be controlled by controlling the laser itself, in some systems it is desirable to control the amount of energy of a laser beam downstream from the laser. Existing systems for laser pulse selection typically have one or more drawbacks, such as power loss, complexity, cost, etc. There is a need for improved systems and methods for laser pulse control.

SUMMARY

The present disclosure is directed to improved systems and methods for dynamically controlling laser pulses being output from a laser system.

In some embodiments, a surgical system comprises: a laser configured to emit electromagnetic radiation in laser pulses; an optical switching device configured to switch between a first condition in which it allows laser pulses emitted from the laser to be output from the laser system and a second condition in which it prevents laser pulses emitted from the laser from being output from the laser system; an adjustable input device configured to be actuated over an operating range; and a laser pulse controller configured to communicate optical switching control signals to the optical switching device, wherein the optical control signals are based on input from the adjustable input device; wherein the operating range of the adjustable input device is configured to allow an operator to control dynamically the laser pulses being output from the laser system.

The operating range of the adjustable input device may be configured to allow an operator to control dynamically the percentage of laser pulses emitted from the laser that are output from the laser system. The optical switching control signals communicated by the laser pulse controller to the optical switching device may comprise a pulse picking rate signal controlling the length of a pulse picking cycle and a pulse control signal controlling the number of laser pulses in each pulse picking cycle to be output from the laser system. The operating range of the adjustable input device may be configured to allow an operator to control dynamically the pulse control signal.

The optical switching device may be configured to control the amount of energy of the laser pulses emitted from the laser that is output from the laser system. The operating range of the adjustable input device may be configured to allow an operator to control dynamically the amount of energy of the laser pulses emitted from the laser that is output from the laser system. The optical switching control signals communicated by the laser pulse controller to the optical switching device may comprise a power level signal controlling the amount of energy of the laser pulses to be output from the laser system. The operating range of the adjustable input device may be configured to allow an operator to control dynamically the power level signal.

The surgical system may be configured to operate in multiple operating modes. In a first operating mode, the operating range of the adjustable input device may be configured to allow an operator to control dynamically the amount of energy of the laser pulses emitted from the laser that is output from the laser system, while in a second operating mode of the surgical system, the operating range of the adjustable input device may be configured to allow an operator to control dynamically the percentage of laser pulses emitted from the laser that are output from the laser system.

The optical switching device may comprise a shutter and a shutter motor. In one example, the shutter motor may be configured to move the shutter in an alternating manner between a first position corresponding to the first condition of the optical switching device and a second position corresponding to the second condition of the optical switching device. The shutter may comprise a mirror. The shutter motor may comprise a galvanometer motor.

In another example, the shutter has an axis of rotation and at least one open area and at least one solid area arranged around the axis of rotation of the shutter, and the shutter motor is configured to rotate the shutter around the axis of rotation of the shutter. In such an example, the first condition of the optical switching device corresponds to a position of the shutter in which a solid area of the shutter is not in a path of the laser pulses emitted from the laser, and the second condition of the optical switching device corresponds to a position of the shutter in which a solid area of the shutter is in the path of the laser pulses emitted from the laser.

The optical switching device may comprise a laser energy control system configured to regulate the amount of electromagnetic energy of each laser pulse that exits the laser system. The laser energy control system may comprise a waveplate, a waveplate motor, and a polarizer plate, wherein the waveplate motor is configured to move the waveplate into different positions corresponding to different percentages of laser electromagnetic energy permitted to pass through the laser energy control system.

In another alternative embodiment, the optical switching device comprises a pockels cell. Like certain other example optical switching devices described herein, such an optical switching device may be capable of picking pulses and adjusting the energy level of pulses.

The adjustable input device may comprise a foot pedal configured to be actuated over the operating range.

In some embodiments, a method of controlling a surgical system comprises: emitting electromagnetic radiation from a laser in laser pulses; actuating an adjustable input device over an operating range to control dynamically the laser pulses being output from the laser system; and outputting laser pulses from the laser system in accordance with input from the adjustable input device. The step of outputting laser pulses from the laser system in accordance with input from the adjustable input device may comprise controlling the percentage of laser pulses emitted from the laser that are output from the laser system. The step of outputting laser pulses from the laser system in accordance with input from the adjustable input device may comprise controlling the amount of energy of the laser pulses emitted from the laser that is output from the laser system.

In some examples, a method of controlling a surgical system may be operated in modes. In a first operating mode of the surgical system, the step of outputting laser pulses from the laser system in accordance with input from the adjustable input device may comprise controlling the amount of energy of the laser pulses emitted from the laser that is output from the laser system. In a second operating mode of the surgical system, the step of outputting laser pulses from the laser system in accordance with input from the adjustable input device may comprise controlling the percentage of laser pulses emitted from the laser that are output from the laser system.

Further examples and features of embodiments of the invention will be evident from the drawings and detailed description.

BRIEF DESCRIPTION OF THE DRAWINGS

The accompanying drawings illustrate example implementations of the systems and methods disclosed herein and, together with the description, serve to explain the principles of the present disclosure.

Figure 1:
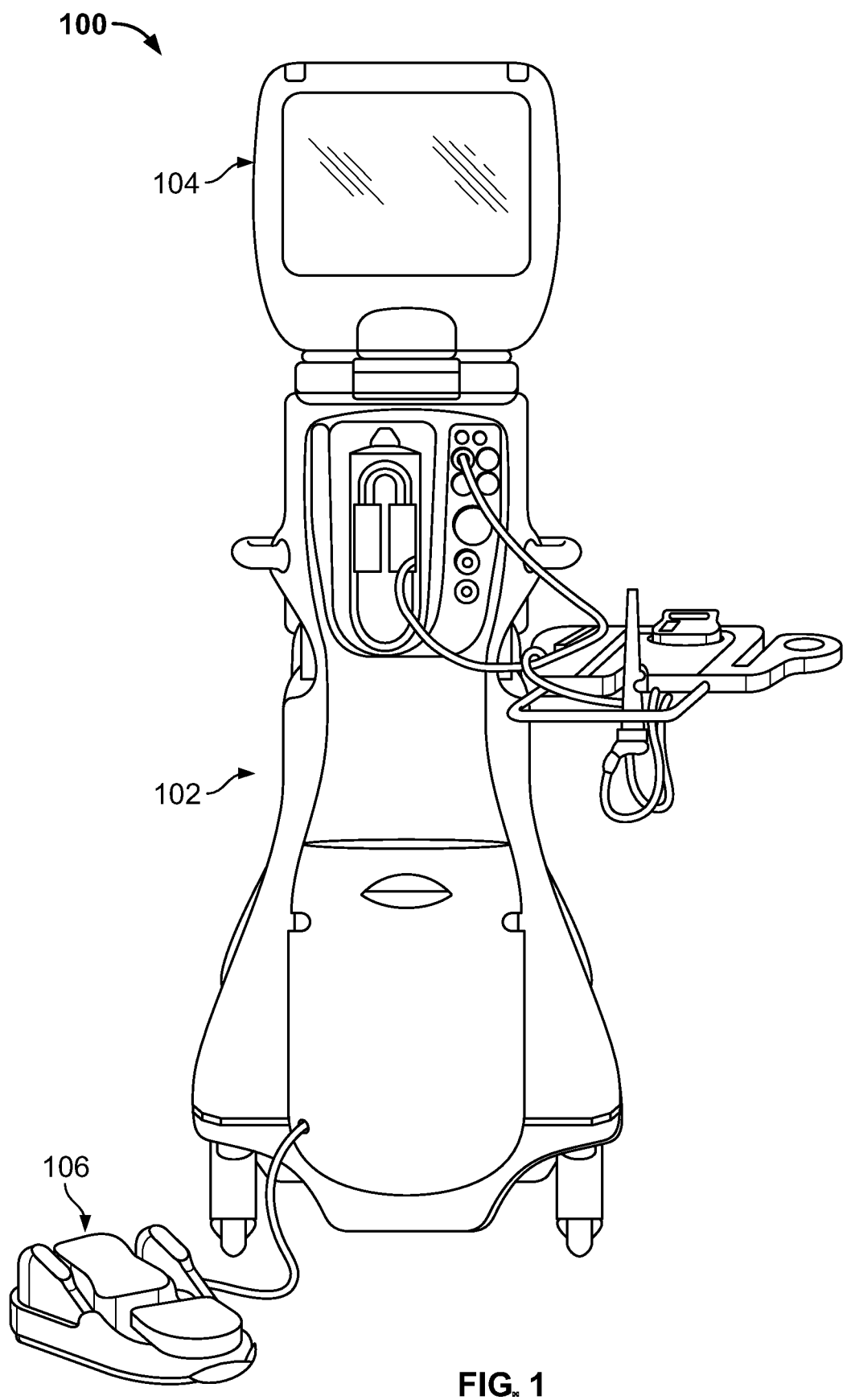
FIG. 1 shows an example ophthalmic surgical console with a foot pedal connected to it.

The accompanying drawings may be better understood by reference to the following detailed description.

DETAILED DESCRIPTION

For the purposes of promoting an understanding of the principles of the disclosure, reference will now be made to the implementations illustrated in the drawings, and specific language will be used to describe those implementations and other implementations. It will nevertheless be understood that no limitation of the scope of the claims is intended by the examples shown in the drawings or described herein. Any alterations and further modifications to the illustrated or described systems, devices, instruments, or methods, and any further application of the principles of the present disclosure, are fully contemplated as would normally occur to one skilled in the art to which the disclosure relates. In particular, the features, components, and/or steps described with respect to one implementation of the disclosure may be combined with features, components, and/or steps described with respect to other implementations of the disclosure. For simplicity, in some instances the same reference numbers are used throughout the drawings to refer to the same or like parts.

The designations "first" and "second" as used herein are not meant to indicate or imply any particular positioning or other characteristic. Rather, when the designations "first" and "second" are used herein, they are used only to distinguish one component from another. The terms "attached," "connected," "coupled," and the like mean attachment, connection, coupling, etc., of one part to another either directly or indirectly through one or more other parts, unless direct or indirect attachment, connection, coupling, etc., is specified.

FIG. 1 shows an example ophthalmic surgical console 100 with a foot pedal 106 connected to it. The example ophthalmic surgical console 100 may be used in systems and methods in accordance with the present disclosure. The ophthalmic surgical console 100 may be similar to ophthalmic surgical consoles as shown and described in U.S. Pat. No. 9,931,447, the entire disclosure of which is hereby expressly incorporated herein by reference. The ophthalmic surgical console 100 may be similar to ophthalmic surgical consoles that have been known and used, such as the CENTURION® Vision System available from Alcon Laboratories, Inc. (Fort Worth, Texas) or the CONSTELLATION® Vision System available from Alcon Laboratories, Inc. (Fort Worth, Texas), or any other ophthalmic surgical console suitable for use with the principles described herein.

As shown in FIG. 1, the example ophthalmic surgical console 100 includes a housing 102 with a computer system disposed therein and an associated display screen 104 showing data relating to system operation and performance during an ophthalmic surgical procedure.

The foot pedal 106 is an adjustable input device that an operator may actuate over an operating range for controlling one or more functions. The foot pedal 106 may be pressed downward to various positions over the operating range to control functioning as described further below. While a foot pedal 106 is shown, other adjustable input devices, such as hand-operated buttons or knobs, may be used. The foot pedal 106 or other adjustable input device may be connected to the surgical console 100 by a wired or wireless connection.

The surgical console 100 includes one or more systems that may be used in performing an ophthalmic surgical procedure. For example, the surgical console 100 may include a fluidics system that includes an irrigation system for delivering fluid to the eye and an aspiration system for aspirating fluid from the eye.

Figure 2:
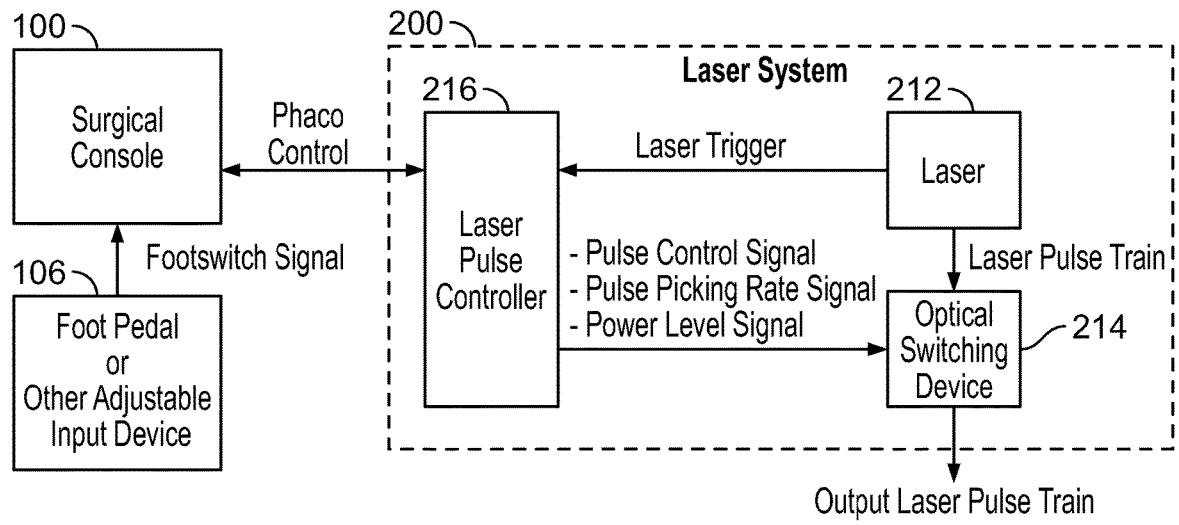
FIG. 2 shows an example of architecture for a surgical system comprising a laser system.

An example surgical system in accordance with this disclosure may include a laser system suitable for one or more ophthalmic procedures. FIG. 2 shows an example of architecture for a surgical system, including a surgical console 100, an adjustable input device, e.g., foot pedal 106, and an example laser system 200. The laser system 200 may comprise a laser 212, an optical switching device 214, and a laser pulse controller 216. In some embodiments, the laser system 200 may be housed within the surgical console 100. In other embodiments, the laser system 200 may be housed in a separate console that communicates with the surgical console 100. In other embodiments, one or more parts of the laser system 200, such as the laser 212 and optical switching device 214, may be housed in a separate console that communicates with the surgical console 100, and one or more other parts of the laser system 200, such as the laser pulse controller 216, may be housed in the surgical console 100. In other embodiments, the laser system 200 may be in a stand-alone housing that receives input from a foot pedal or other adjustable input device 106 without the need for a separate surgical console 100.

In addition to the laser 212, optical switching device 214, and laser pulse controller 216, the laser system 200 may have other components. For example, the laser system 200 may include components for operating the laser, such as a power supply, laser pumps, laser energy control, and monitor. In addition, the laser system 200 may include other components in the optical path of the laser output, such as one or more lenses, mirrors, and optical fibers (not shown).

In some embodiments, the laser system 200 may be suitable for cataract surgery. In some embodiments, the output energy of the laser system is suitable for fragmentation and/or emulsification a cataractous lens. In some examples, the laser output is used for fragmentation and/or phacoemulsification of the lens to a sufficient degree for removal of the lens.

The laser 212 may be any type of laser suitable for the desired application. The laser 212 may output suitable electromagnetic radiation at any suitable wavelength. For example, the laser 212 may emit electromagnetic radiation in one or more wavelengths in the visible, infrared, and/or ultraviolet wavelengths. The laser 212 may operate or be operated to emit a continuous beam of electromagnetic radiation. Alternatively, the laser 212 may operate or be operated to emit a pulsed beam.

In one example, the laser 212 operates in the infrared range. For example, the laser 212 may output electromagnetic radiation in the mid-infrared range, for example in a range of about 2.0 microns to about 4.0 microns. Some examples wavelengths include about 2.5 microns to 3.5 microns, such as about 2.775 microns, about 2.8 microns, or about 3.0 microns. Such a laser may be suitable, for example, for lens fragmentation in cataract surgery, or for other procedures.

The laser system 200 is designed to direct the laser electromagnetic radiation from the laser 212 to an output port. The laser system 200 may direct the laser electromagnetic radiation from the laser 212 to the output port through one or more optical components, such as lenses and mirrors.

An instrument may be optically connected to the laser system 200 to receive the laser electromagnetic radiation from the output port. The instrument may be, for example, a handpiece for an ophthalmic procedure. The instrument or handpiece may be connected to the laser system by a delivery optical fiber. The delivery optical fiber may be flexible and relatively long to give the operator flexibility in maneuvering the handpiece at some distance away from the laser system 200. The laser electromagnetic radiation may be transmitted from the laser system 200, through the optical fiber and handpiece, and from an output tip of the handpiece to the desired target, such as a lens or lens fragment in the eye of a patient.

The optical switching device 214 is a device that operates either to allow laser electromagnetic radiation, e.g., laser pulses, emitted from the laser 212 to be output from the laser system or to prevent laser electromagnetic radiation, e.g., laser pulses, emitted from the laser 212 from being output from the laser system. The optical switching device 214 may switch back and forth between these two conditions, under the control of the laser pulse controller 216.

In some examples, the optical switching device 214 may comprise a shutter and a shutter motor. Examples of suitable optical switching devices are described and illustrated in U.S. Provisional Patent Application No. 63/186,387, the entirety of which is hereby incorporated by reference herein, and in U.S. Provisional Patent Application No. 63/222,521, the entirety of which is hereby incorporated by reference herein.

For example, the optical switching device 214 may comprise a shutter that is moved by the shutter motor into and out of the path of laser electromagnetic radiation, to selectively allow or prevent laser electromagnetic radiation from being output from the laser system. The shutter motor may be configured to move the shutter in an alternating manner between a first position corresponding to a first condition of the optical switching device (in which it allows laser electromagnetic energy, e.g., laser pulses, emitted from the laser to be output from the laser system) and a second position corresponding to a second condition of the optical switching device (in which it prevents laser electromagnetic energy, e.g., laser pulses, emitted from the laser from being output from the laser system). In an example, the shutter comprises a mirror, and the shutter motor comprises a galvanometer motor.

In another example, the optical switching device 214 may comprise: (i) a shutter having an axis of rotation and at least one open area and at least one solid area arranged around the axis of rotation of the shutter, and (ii) a shutter motor configured to rotate the shutter around the axis of rotation of the shutter. In such an example, the first condition of the optical switching device (in which it allows laser electromagnetic energy, e.g., laser pulses, emitted from the laser to be output from the laser system) corresponds to a position of the shutter in which a solid area of the shutter is not in a path of the laser pulses emitted from the laser, and the second condition of the optical switching device (in which it prevents laser electromagnetic energy, e.g., laser pulses, emitted from the laser from being output from the laser system) corresponds to a position of the shutter in which a solid area of the shutter is in the path of the laser pulses emitted from the laser.

The optical switching device 214 may further comprise a laser energy control system configured to regulate the amount of electromagnetic energy of each laser pulse that exits the laser system. For example, the laser energy control system may comprise a waveplate, a waveplate motor, and a polarizer plate, wherein the waveplate motor is configured to move the waveplate into different positions corresponding to different percentages of laser electromagnetic energy permitted to pass through the laser energy control system. Examples of such laser energy control systems are described and illustrated in U.S. Provisional Patent Application No. 63/186,387, the entirety of which is hereby incorporated by reference herein, and in U.S. Provisional Patent Application No. 63/222,521, the entirety of which is hereby incorporated by reference herein.

In another alternative embodiment, the optical switching device 214 may comprise a pockels cell. A pockels cell optical switching device may switch back and forth, under the control of the laser pulse controller 216, between a first condition in which it allows laser pulses emitted from the laser to be output from the laser system and a second condition in which it prevents laser pulses emitted from the laser from being output from the laser system. Also, a pockels cell optical switching device can be operated incrementally to allow different percentages of electromagnetic energy emitted by the laser to be output by the laser system.

The laser pulse controller 216 is configured to communicate optical switching control signals to the optical switching device 214. The optical control signals are based on inputs to the surgical system, including from the adjustable input device, e.g., foot pedal 106.

Figure 3:
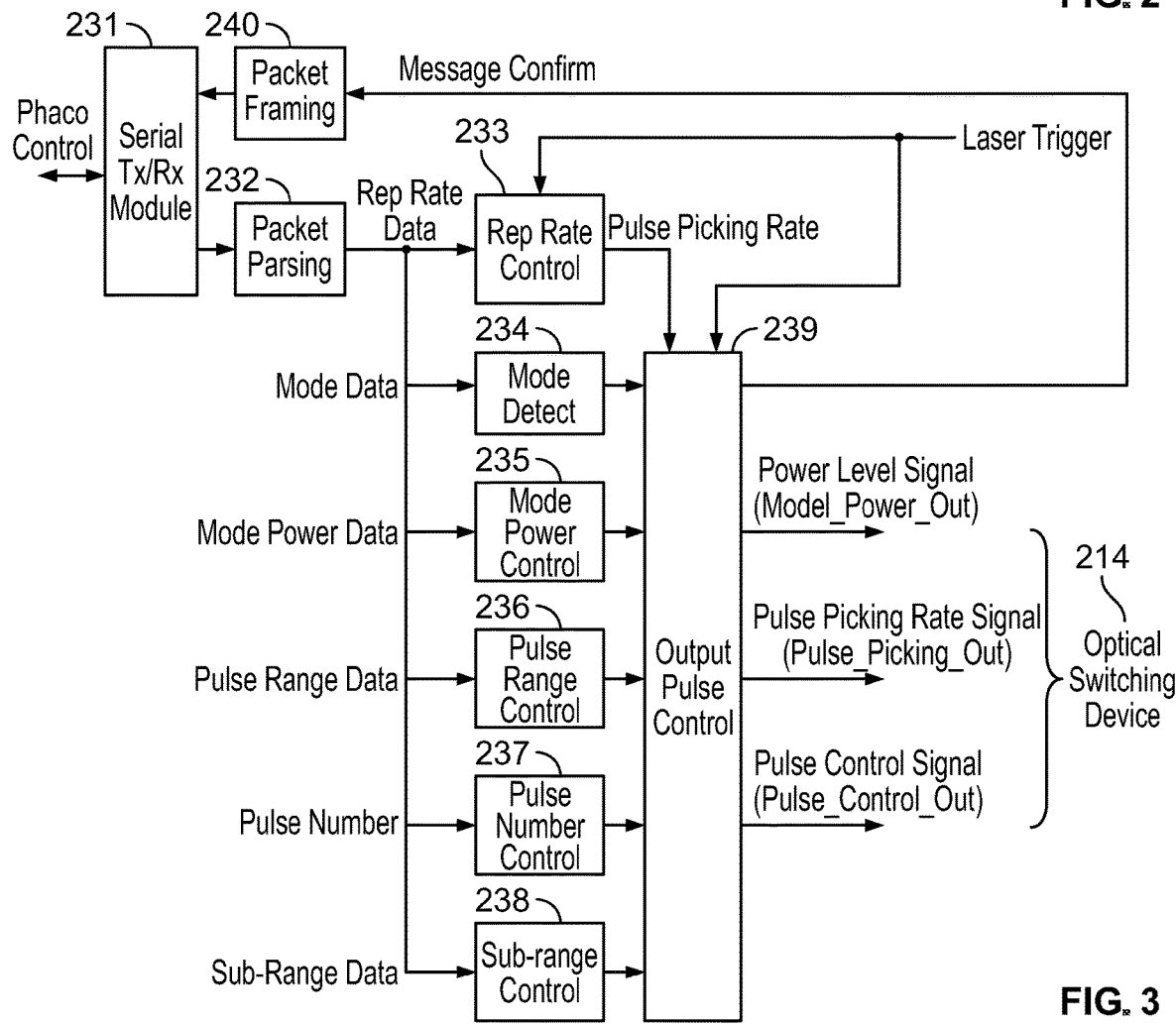
FIG. 3 shows an example of architecture for a laser pulse controller.

FIG. 3 shows an example of architecture for a laser pulse controller 216. As would be understood by persons having ordinary skill in the art, the use of controllers in processing environments may be implemented in software, firmware, hardware or some suitable combination of software, firmware, and/or hardware, such as software loaded into a processor and executed. The laser pulse controller 216 may be implemented in software, firmware, hardware or some suitable combination of software, firmware, and/or hardware, such as software loaded into a processor and executed.

The example laser pulse controller 216 comprises a serial transmitter/receiver (Tx/Rx) module 231 that communicates with a serial communication (Tx/Rx) controller or similar device (e.g., similar Ethernet device) of the surgical console 100. In use, the surgical console 100 sends packets of data to the laser pulse controller 216, which are received by the serial Tx/Rx module 231. As described in more detail below, the packets include data based, at least in part, on input from the adjustable input device 106. A packet parsing module 232 of the laser pulse controller 216 is configured to parse the packet data. In the illustrated example, the packet parsing module 232 sends repetition rate data and pulse picking rate data to a repetition rate control module 233, mode data to a mode detect module 234, mode power data to a mode power control module 235, pulse range data to a pulse range control module 236, pulse number data to a pulse number control module 237, and sub-range data to a sub-range control module 238. The repetition rate control module 233 also receives a laser trigger input signal, indicating the beginning of each laser pulse. The repetition rate control module 233 send signals indicating pulse picking rate to an output pulse control module 239, which may also receive a laser trigger input signal. The output pulse control module 239 also receives input signals from the mode detect module 234, mode power control module 235, pulse range control module 236, pulse number control module 237, and sub-range control module 238 based on their respective input data.

The output pulse control module 239 of the laser pulse controller 216 sends optical switching control signals to the optical switching device 214, wherein the optical switching control signals are based, at least in part, on input from the adjustable input device 106. The optical switching control signals communicated by the laser pulse controller 216 to the optical switching device 214 may comprise a pulse picking rate signal (e.g., Pulse_Picking_Out), which controls the length of a pulse picking cycle, and a pulse control signal (e.g., Pulse_Control_Out), which controls the number of laser pulses in each pulse picking cycle to be output from the laser system. The optical switching control signals communicated by the laser pulse controller 216 to the optical switching device 214 may also comprise a power level signal (e.g., Mode_Power_Out), which controls the amount of energy of the laser pulses to be output from the laser system.

The output pulse control module 239 of the laser pulse controller 216 may also send message confirm signals to a packet framing module 240. The packet framing module 240 assembles the data from the message confirm signal and sends it as packets of data to the serial Tx/Rx module 231. The Tx/Rx module 231 then sends the packets of data based on the message confirm signals to the serial Tx/Rx controller of the surgical console 100 to confirm the signals from the laser pulse controller 216.

Figure 4:
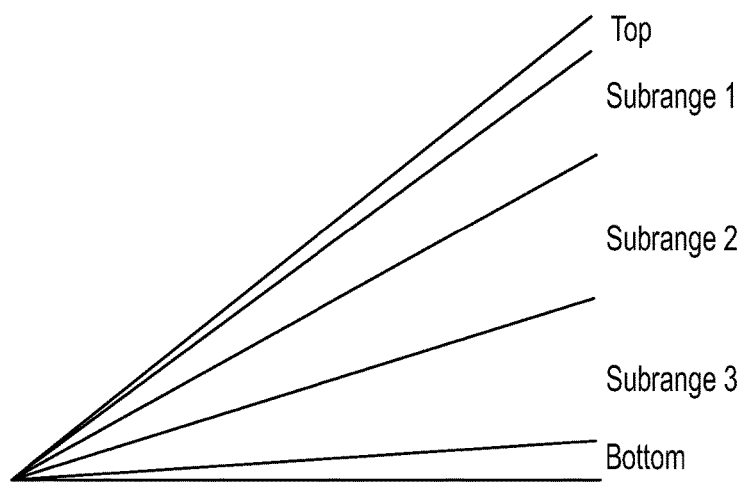
FIG. 4 shows an example operating range for an adjustable input device such as a foot pedal.

FIG. 4 shows an example operating range for an adjustable input device such as a foot pedal 106. The foot pedal 106 or other adjustable input device can be actuated by an operator over the operating range to control the laser output. In the example of a foot pedal, the operator depresses the foot pedal by the desired amount to move the foot pedal into the desired area of the operating range. In other examples, such as hand-operated buttons or knobs, the operator moves or tunes the input device into the desired area of the operating range. The foot pedal or other adjustable input device is adjustable in real time during a surgical procedure, giving the operator the ability to dynamically control the laser pulses being output from the laser system during a procedure.

Many examples of different functioning over the operating range are possible. In the illustrated example, the operating range includes three subranges, but more or fewer subranges may be used.

The following is a description of one of many examples. When the adjustable input device is moved or tuned to subrange 1, the surgical console may be activated for a specific function, such as irrigation, without any laser output. When the adjustable input device is moved or tuned to subrange 2, the surgical console may be activated for a different function, such as aspiration, without any laser output. The irrigation function may continue to operate in subrange 2. When the adjustable input device is moved or tuned to subrange 3, the laser system may be activated to output laser electromagnetic energy. The irrigation and/or aspiration functions may continue to operate in subrange 3. By moving or tuning the adjustable input device within subrange 3, the operator may dynamically adjust the laser output, as described below.

Many variations are possible. For example, subrange 2 and 3 in the above example may be reversed, such that laser control occurs in subrange 2 and aspiration occurs in subrange 3.

In one example, the laser system may have multiple operating modes. In a first operating mode, "sculpt" mode, the laser system is operated to output all laser pulses emitted by the laser, while the adjustment of the adjustable input device controls the percentage of electromagnetic energy of the laser pulses that are output. That is, the laser emits laser pulses at a specific energy, and the input from the adjustable input device is used to adjust the laser energy control system of the optical switching device 214 to control the percentage of energy of the laser pulses that are output from the laser system. Based on the input from the adjustable input device, the power level signal (e.g., Mode_Power_Out), which is sent by the laser pulse controller 216 to the optical switching device 214, is adjusted to control the amount of energy of the laser pulses output from the laser system. For example, the top of subrange 3 may correspond to 0% of laser energy output, the bottom of subrange 3 may correspond to 100% of laser energy output, and positions in between may correspond to increments in the range of 0% to 100%. When operating in sculpt mode, the operator can control the amount of laser electromagnetic energy of each pulse that is output from the laser system by adjusting the adjustable input device within subrange 3.

In a second mode, "quad" mode, the laser system is operated to output only certain of the laser pulses emitted by the laser, with the adjustment of the adjustable input device controlling which laser pulses are output. That is, the laser emits laser pulses at a specific repetition rate, and the input from the adjustable input device is used to control the optical switching device 214 to switch back and forth between the first condition in which it allows laser pulses emitted from the laser to be output from the laser system and the second condition in which it prevents laser pulses emitted from the laser from being output from the laser system.

For example, the top of subrange 3 may correspond to none of the laser pulses being output, the bottom of subrange 3 may correspond to the maximum number of laser pulses being output (as permitted by the selected pulse picking rate, as explained in more detail below), and positions in between are increments in the range of 0 to the maximum. When operating in quad mode, the operator can control the percentage of laser pulses that are output from the laser system by adjusting the adjustable input device within subrange 3.

In certain embodiments, a pulse picking rate may be selected, which controls the length of a pulse picking cycle. The adjustable input device may be used to control the pulse control signal, which is sent by the laser pulse controller to the optical switching device and controls the number of laser pulses in each pulse picking cycle to be output from the laser system. For example, if the repetition rate of the laser is 1000 Hz, a pulse picking rate of 125 Hz allows at maximum four out of every eight laser pulses from the laser to be output from the laser system. Within each cycle of the pulse picking rate of 125 Hz, the maximum number of pulses that may be output is 4. In this example, when operating in quad mode, the operator can use the adjustable input device to select how many of these pulses in each cycle, i.e., 0, 1, 2, 3, or 4, to be output from the laser system, thereby controlling the percentage of laser pulses that are output. Based on the input from the adjustable input device, the laser pulse controller 216 sends to the optical switching device 214 a pulse control signal (e.g., Pulse_Control_Out), which controls the number of laser pulses in each pulse picking cycle to be output from the laser system, from 0 to 4 in this example. This example and other examples are illustrated in FIGS. 7 to 13 and are described further below.

The operating mode (e.g., sculpt mode, quad mode) may be selected by the adjustable input device or another input device. For example, a button, knob, or touchscreen may be used for selecting the operating mode. In addition, the pulse picking rate may be selected by the adjustable input device or another input device, such as a button, knob, or touchscreen. The repetition rate of the laser and the energy output of the laser, including different energy outputs of the laser for different operating modes, if desired, may also be selected by the adjustable input device or another input device, such as a button, knob, or touchscreen.

In one example, different operating modes may be selectable within the operating range of the adjustable input device. For example, the top of subrange 3 in the above example may correspond to sculpt mode, while the bottom of subrange 3 in the above example may correspond to quad mode.

Figure 5:
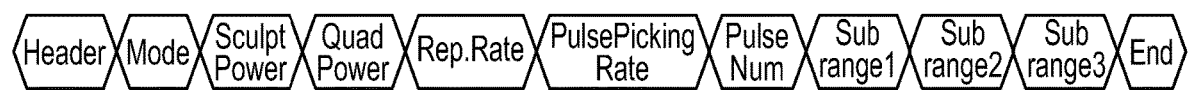
FIG. 5 shows an example packet of instructions for sending to a laser pulse controller.

FIG. 5 shows an example packet of instructions for sending to a laser pulse controller. The packet includes the following data: Header, Mode, Sculpt Power, Quad Power, Repetition Rate, Pulse Picking Rate, Pulse Number, Subrange 1, Subrange 2, Subrange 3, and End. The Header identifies the beginning of the packet. The Mode identifies which operating mode has been selected, e.g., sculpt mode or quad mode. The Sculpt Power identifies the selected power output of the laser during sculpt mode. The Quad Power identifies the selected power output of the laser during quad mode. The Repetition Rate identifies the rate of pulses to be emitted from the laser. The Pulse Picking Rate identifies the length of a pulse picking cycle. The Pulse Number identifies the maximum number of laser pulses that may be selected in each pulse picking cycle. Subrange 1, Subrange 2, and Subrange 3 identify the position to which the adjustable input device has been moved or tuned, including the incremental position within the range (e.g., 0 to 100).

Figure 6:
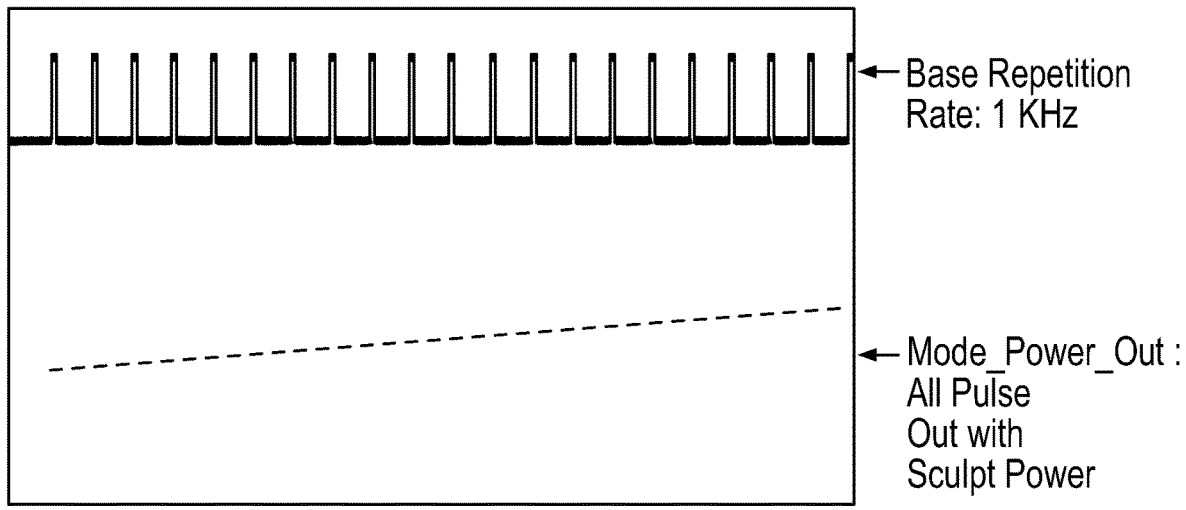
FIG. 6 shows example signals from a laser pulse controller for operating a laser surgical system in a first mode.

FIG. 6 shows example signals from a laser pulse controller for operating a laser surgical system in a first mode, which in this example corresponds to sculpt mode, as described above. The top line in FIG. 6 shows the repetition rate of the laser pulses being emitted by the laser, which in this example is 1 KHz. In sculpt mode, all of the laser pulses emitted by the laser are output from the laser system, while the operator's adjustment of the adjustable input device controls the percentage of electromagnetic energy of the laser pulses that are output. Based on the input from the adjustable input device, the power level signal (Mode_Power_Out), which is sent by the laser pulse controller to the optical switching device, is adjusted to control the amount of energy of the laser pulses output from the laser system. The bottom line in FIG. 6 shows the power level signal (Mode_Power_Out). At the left end of the line, 0% of the laser energy is being output. At the right end of the line, 100% of the laser energy is being output. Positions in between correspond to increments in the range of 0% to 100% of the laser energy being output.

Figure 7:
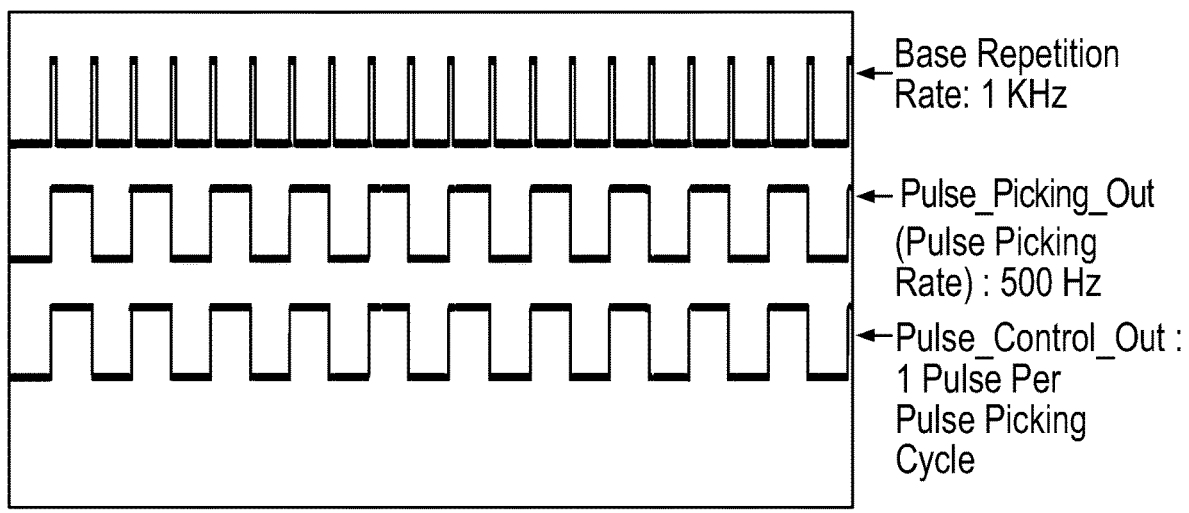
FIG. 7 shows an example of signals from a laser pulse controller for operating a laser surgical system in a second mode, including an example pulse picking rate signal and pulse control signal.

FIG. 7 shows an example of signals from a laser pulse controller for operating a laser surgical system in a second mode, which in this example corresponds to quad mode, as described above. The top line in FIG. 7 shows the repetition rate of the laser pulses being emitted by the laser, which in this example is 1 KHz. The middle and bottom lines in FIG. 7 show the pulse picking rate signal (Pulse_Picking_Out) and pulse control signal (Pulse_Control_Out), respectively, that are sent by the laser pulse controller to the optical switching device. The pulse picking rate controls the length of the pulse picking cycle. For example, the pulse picking rate in FIG. 7 is 500 Hz, which corresponds to one cycle for every two laser pulses emitted by the laser. Each cycle of this pulse picking rate permits, at maximum, one laser pulse to be output from the system. The adjustable input device may be used to control the pulse control signal, which controls the number of laser pulses in each pulse picking cycle to be output from the laser system. With the repetition rate of 1 KHz and pulse picking rate of 500 Hz, the pulse control rate may be adjusted based on input from the adjustable input device (e.g., foot pedal) to 0 pulses per cycle or 1 pulse per cycle. In FIG. 7, the pulse control signal is at its maximum, the full extent of the pulse picking rate, such that one pulse out of every cycle of the pulse picking rate is output from the laser system. This corresponds to a laser pulse output rate of 500 KHz.

Figure 8:
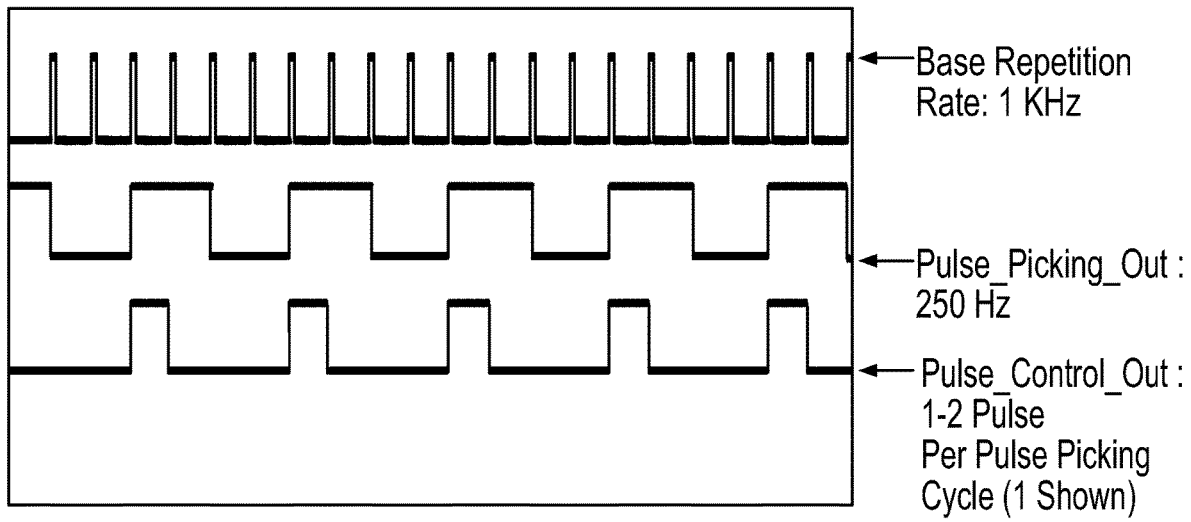
FIG. 8 shows another example of signals from a laser pulse controller for operating a laser surgical system in a second mode, including another example pulse picking rate signal and pulse control signal.

FIG. 8 shows another example of signals from a laser pulse controller for operating a laser surgical system in quad mode. The top line in FIG. 8 shows the repetition rate of the laser pulses being emitted by the laser, which in this example is 1 KHz. The middle and bottom lines in FIG. 8 show the pulse picking rate signal (Pulse_Picking_Out) and pulse control signal (Pulse_Control_Out), respectively, that are sent by the laser pulse controller to the optical switching device. The pulse picking rate in FIG. 8 is 250 Hz, which corresponds to one cycle for every four laser pulses emitted by the laser. Each cycle of this pulse picking rate permits, at maximum, two laser pulses to be output from the system. With the repetition rate of 1 KHz and pulse picking rate of 250 Hz, the pulse control rate may be adjusted based on input from the adjustable input device (e.g., foot pedal) to 0, 1, or 2 pulses per cycle. In FIG. 8, the pulse control signal is at 1 pulse per cycle. This corresponds to a laser pulse output rate of 250 KHz.

Figure 9:
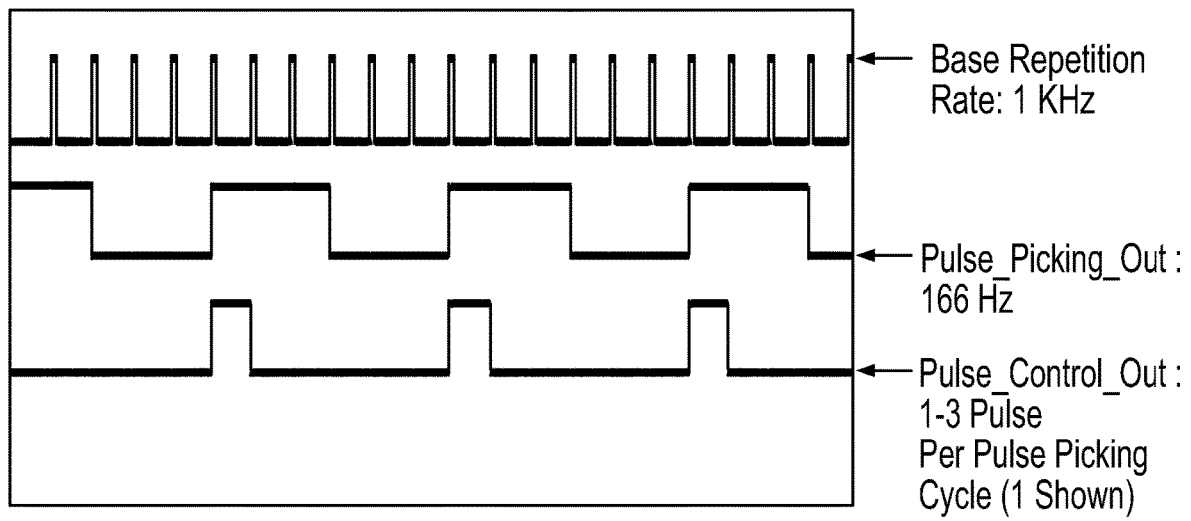
FIG. 9 shows another example of signals from a laser pulse controller for operating a laser surgical system in a second mode, including another example pulse picking rate signal and pulse control signal.

FIG. 9 shows another example of signals from a laser pulse controller for operating a laser surgical system in quad mode. The top line in FIG. 9 shows the repetition rate of the laser pulses being emitted by the laser, which in this example is 1 KHz. The middle and bottom lines in FIG. 9 show the pulse picking rate signal (Pulse_Picking_Out) and pulse control signal (Pulse_Control_Out), respectively, that are sent by the laser pulse controller to the optical switching device. The pulse picking rate in FIG. 9 is 166 Hz, which corresponds to one cycle for every six laser pulses emitted by the laser. Each cycle of this pulse picking rate permits, at maximum, three laser pulses to be output from the system. With the repetition rate of 1 KHz and pulse picking rate of 166 Hz, the pulse control rate may be adjusted based on input from the adjustable input device (e.g., foot pedal) to 0, 1, 2, or 3 pulses per cycle. In FIG. 9, the pulse control signal is at 1 pulse per cycle. This corresponds to a laser pulse output rate of 166 KHz.

Figure 10:
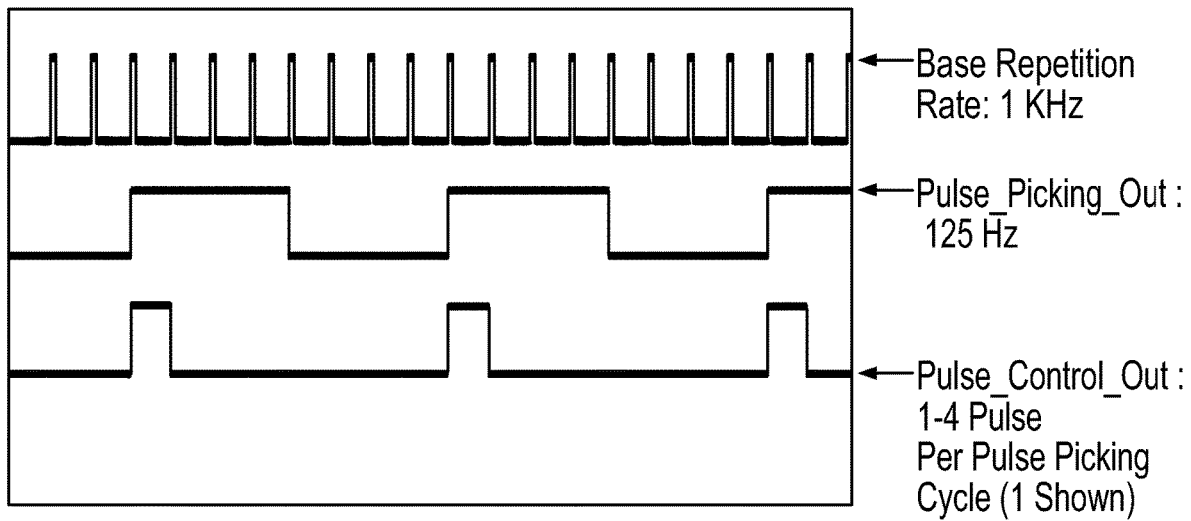
FIG. 10 shows another example of signals from a laser pulse controller for operating a laser surgical system in a second mode, including another example pulse picking rate signal and pulse control signal.

FIG. 10 shows another example of signals from a laser pulse controller for operating a laser surgical system in quad mode. The top line in FIG. 10 shows the repetition rate of the laser pulses being emitted by the laser, which in this example is 1 KHz. The middle and bottom lines in FIG. 10 show the pulse picking rate signal (Pulse_Picking_Out) and pulse control signal (Pulse_Control_Out), respectively, that are sent by the laser pulse controller to the optical switching device. The pulse picking rate in FIG. 10 is 125 Hz, which corresponds to one cycle for every eight laser pulses emitted by the laser. Each cycle of this pulse picking rate permits, at maximum, four laser pulses to be output from the system. With the repetition rate of 1 KHz and pulse picking rate of 125 Hz, the pulse control rate may be adjusted based on input from the adjustable input device (e.g., foot pedal) to 0, 1, 2, 3, or 4 pulses per cycle. In FIG. 10, the pulse control signal is at 1 pulse per cycle. This corresponds to a laser pulse output rate of 125 KHz. In this example, in each cycle of eight laser pulses emitted from the laser, the optical switching device allows one laser pulse to be output from the laser system and prevents the following seven laser pulses from being output from the laser system.

Figure 11:
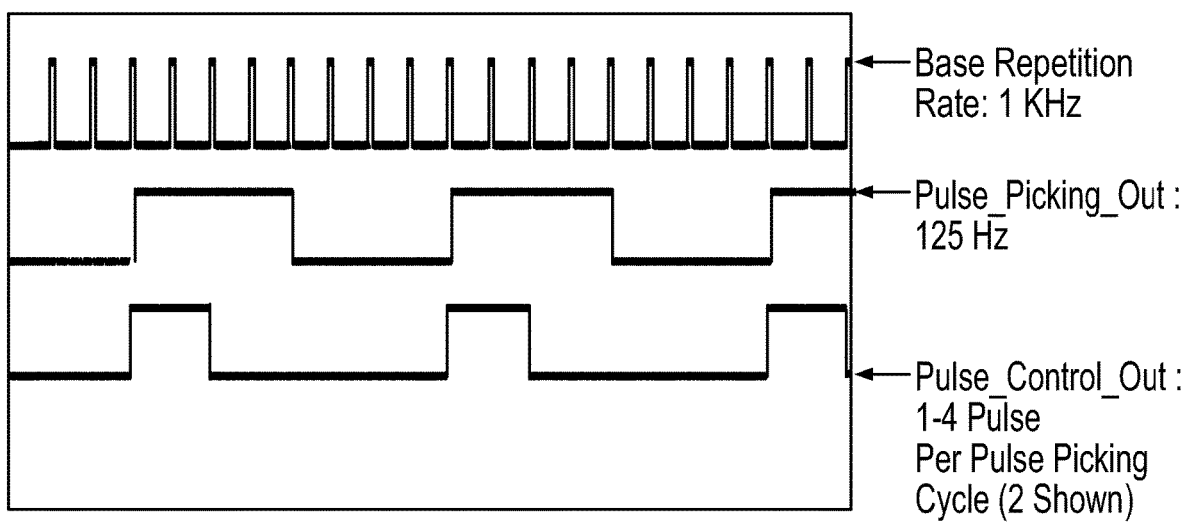
FIG. 11 shows another example of signals from a laser pulse controller for operating a laser surgical system in a second mode, with the same example pulse picking rate signal as in FIG. 10 but with a different pulse control signal.

FIG. 11 shows an example similar to FIG. 10, except the pulse control rate has been adjusted based on input from the adjustable input device (e.g., foot pedal) to allow 2 pulses per cycle to be output from the laser system. In this example, in each cycle of eight laser pulses emitted from the laser, the optical switching device allows two laser pulses to be output from the laser system and prevents the following six laser pulses from being output from the laser system.

Figure 12:
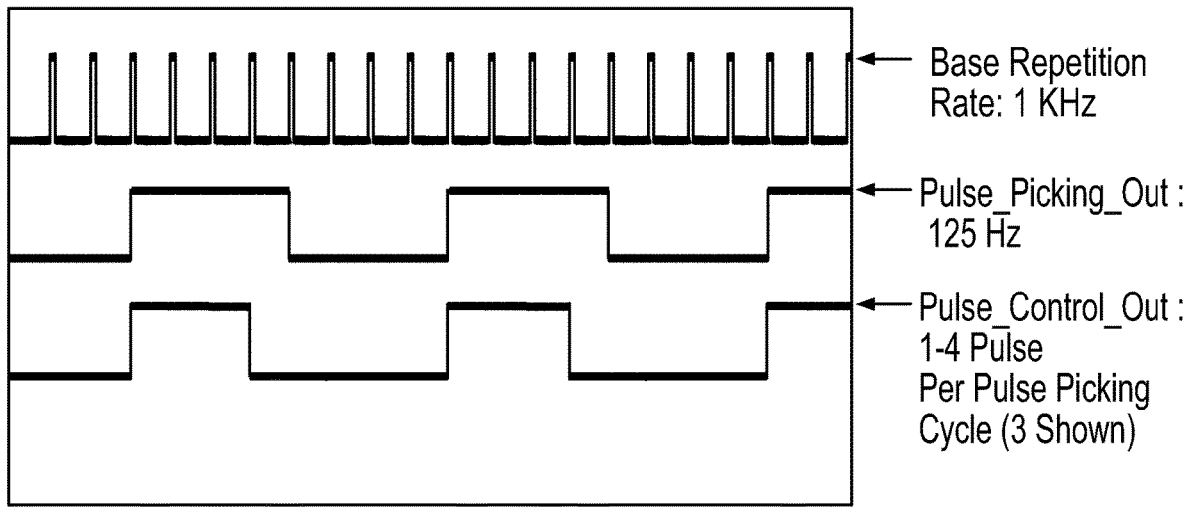
FIG. 12 shows another example of signals from a laser pulse controller for operating a laser surgical system in a second mode, with the same example pulse picking rate signal as in FIGS. 10 and 11 but with a different pulse control signal.

FIG. 12 shows an example similar to FIG. 10, except the pulse control rate has been adjusted based on input from the adjustable input device (e.g., foot pedal) to allow 3 pulses per cycle to be output from the laser system. In this example, in each cycle of eight laser pulses emitted from the laser, the optical switching device allows three laser pulse to be output from the laser system and prevents the following five laser pulses from being output from the laser system.

Figure 13:
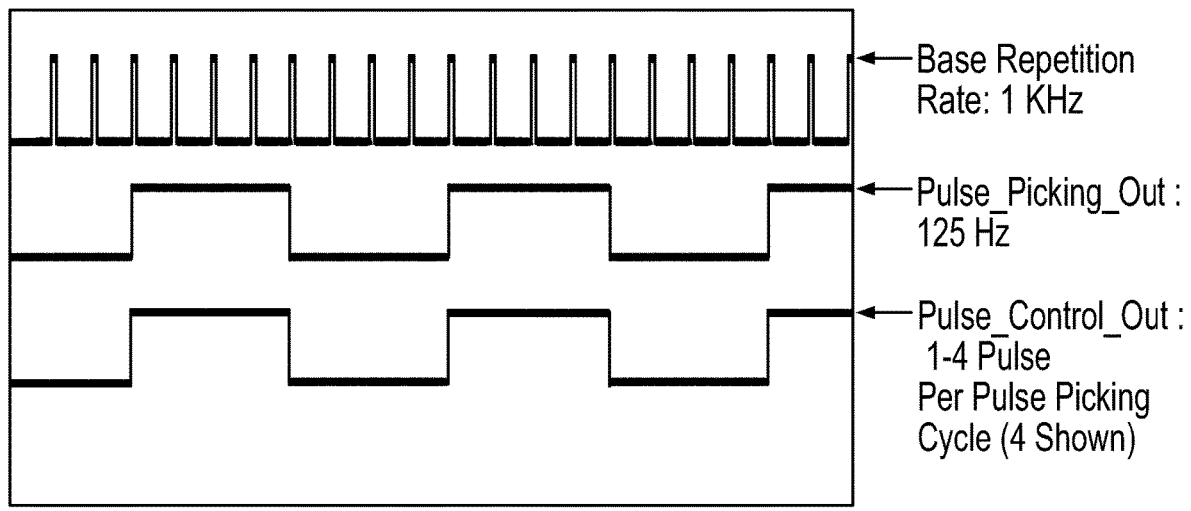
FIG. 13 shows another example of signals from a laser pulse controller for operating a laser surgical system in a second mode, with the same example pulse picking rate signal as in FIGS. 10, 11, and 12 but with a different pulse control signal.

FIG. 13 shows an example similar to FIG. 10, except the pulse control rate has been adjusted based on input from the adjustable input device (e.g., foot pedal) to allow 4 pulses per cycle to be output from the laser system. In this example, in each cycle of eight laser pulses emitted from the laser, the optical switching device allows four laser pulses to be output from the laser system and prevents the following four laser pulses from being output from the laser system.

The maximum number of pulses that may be selected for output in each pulse picking cycle is based on both the repetition rate of the laser and the pulse picking rate. The following table shows, for repetition rates of 1100 Hz, 1000 Hz, and 900 Hz, and for certain example pulse picking rates, how adjustment of the pulse picking rate changes the maximum number of pulses that may be selected for output in each pulse picking cycle:

| Repetition Rate 1100 Hz | | Repetition Rate 1000 Hz | | Repetition Rate 900 Hz | |
|---|---|---|---|---|---|
| Pulse Picking Rate (Hz) | Max Pulses | Pulse Picking Rate (Hz) | Max Pulses | Pulse Picking Rate (Hz) | Max Pulses |
| 1100 | 1100 | 1000 | 1000 | 900 | 900 |
| 550 | 1 | 500 | 1 | 450 | 1 |
| 275 | 2 | 250 | 2 | 225 | 2 |
| 183 | 3 | 166 | 3 | 150 | 3 |
| 137 | 4 | 125 | 4 | 112 | 4 |
| 110 | 5 | 100 | 5 | 90 | 5 |
| 91 | 6 | 83 | 6 | 75 | 6 |
| 78 | 7 | 71 | 7 | 64 | 7 |
| 68 | 8 | 62 | 8 | 56 | 8 |
| 61 | 9 | 55 | 9 | 50 | 9 |
| 55 | 10 | 50 | 10 | 40 | 11 |
| 50 | 11 | 40 | 12 | 30 | 15 |
| 40 | 14 | 30 | 17 | 20 | 22 |
| 30 | 18 | 20 | 24 | 10 | 45 |
| 20 | 27 | 10 | 50 | | |
| 10 | 55 | | | | |

Any repetition rate suitable for the desired application may be used. As additional examples, the following table shows, for repetition rates of 1500 Hz and 2000 Hz, and for certain example pulse picking rates, how adjustment of the pulse picking rate changes the maximum number of pulses that may be selected for output in each pulse picking cycle:

| Repetition Rate 1500 Hz | | Repetition Rate 2000 Hz | |
|---|---|---|---|
| Pulse Picking Rate (Hz) | Max Pulses | Pulse Picking Rate (Hz) | Max Pulses |
| 1500 | 1500 | 2000 | 2000 |
| 750 | 1 | 1000 | 1 |
| 375 | 2 | 500 | 2 |
| 250 | 3 | 250 | 4 |
| 150 | 5 | 200 | 5 |
| 125 | 6 | 125 | 8 |
| 75 | 10 | 100 | 10 |
| 50 | 15 | 50 | 20 |
| 30 | 25 | 40 | 25 |
| 25 | 30 | 25 | 40 |
| 15 | 50 | 20 | 50 |
| | | 10 | 100 |

By selecting and/or adjusting the repetition rate, pulse picking rate, and pulse control signal, any desired sequence of allowing laser pulses to be output and preventing laser pulses from being output may be selected. The adjustable input device and systems and methods disclosed herein enable the operator to have dynamic control over laser pulse output.

An example method of controlling a surgical system as described herein is as follows. An operator selects inputs for the operating mode (e.g., sculpt mode or quad mode), sculpt power (maximum power during sculpt mode), quad power, repetition rate of the laser, and pulse picking rate. Alternatively, any of these parameters may be preset. The operator operates the system, with the laser output of a handpiece directed at the desired location (e.g., a cataractous lens). The laser emits electromagnetic radiation from a laser in laser pulses. The operator actuates the adjustable input device (e.g., foot pedal) over an operating range to control dynamically the laser pulses being output from the laser system.

The input from the adjustable input device, and other parameters, are sent (e.g., by a packet as in FIG. 5) to a laser pulse controller. Based on the input, the laser pulse controller sends optical switching control signals to the optical switching device to control the laser output.

In a sculpt operating mode, the optical switching control signals may comprise a power level signal controlling the amount of energy of the laser pulses to be output from the laser system. The power level signal is based on dynamic input from the adjustable input device. The operator may dynamically adjust the adjustable input device in real time to adjust the power level signal and, consequently, the amount of energy of the laser pulses to be output from the laser system.

In a quad operating mode, the optical switching control signals may comprise a pulse picking rate signal controlling the length of a pulse picking cycle and a pulse control signal controlling the number of laser pulses in each pulse picking cycle to be output from the laser system. The pulse control signal is based on dynamic input from the adjustable input device. The operator may dynamically adjust the adjustable input device in real time to adjust the pulse control signal and, consequently, the number of laser pulses in each pulse picking cycle to be output from the laser system. In this manner, the operator may adjust the percentage of laser pulses emitted from the laser that are output from the laser system.

The operator may switch between operating modes. The selected operating mode may be based on the type of procedure, the stage of the procedure, the conditions, or other factors.

The ability to selectively output laser pulses and/or to control the laser output energy is useful for procedures in which laser control is advantageous. For example, in cataract surgery, it may be desirable to operate the laser system with high power for initially breaking up the lens, so sculpt mode may be preferred. It may be desirable to operate the laser system with lower power for breaking up smaller pieces, so a lower energy level in sculpt mode or quad mode may be preferred. Pulse number control and/or pulse energy level control of laser pulses allows for a correct level of force to be applied to smaller particles which might otherwise be pushed away before they can be aspirated out of the eye by the irrigation system of the hand piece.

As would be understood by persons of ordinary skill in the art, systems and methods as disclosed herein have advantages over prior systems and methods. For example, systems and methods as described herein allow simple and dynamic control of laser pulses and energy, improving the ease, time, efficiency, accuracy, outcome, and/or cost of the procedures.

Persons of ordinary skill in the art will appreciate that the embodiments encompassed by the disclosure are not limited to the particular example embodiments described above. While illustrative embodiments have been shown and described, a wide range of modification, change, and substitution is contemplated in the foregoing disclosure. It is understood that such variations may be made to the foregoing without departing from the scope of the disclosure. Accordingly, it is appropriate that the appended claims be construed broadly and in a manner consistent with the disclosure.

What is claimed is:
1. A surgical system comprising:
   a laser configured to emit electromagnetic radiation in laser pulses;
   an optical switching device configured to switch between a first condition in which it allows laser pulses emitted from the laser to be output from the surgical system and a second condition in which it prevents laser pulses emitted from the laser from being output from the surgical system;

an adjustable input device configured to be actuated over an operating range; and a laser pulse controller configured to communicate optical switching control signals to the optical switching device, wherein the optical switching control signals are based on input from the adjustable input device;

wherein the operating range of the adjustable input device is configured to allow an operator to control dynamically the laser pulses being output from the surgical system;

wherein the operating range of the adjustable input device is configured to allow an operator to control dynamically a percentage of laser pulses emitted from the laser that are output from the surgical system;

wherein the optical switching control signals communicated by the laser pulse controller to the optical switching device comprise a pulse picking rate signal controlling a length of a pulse picking cycle and a pulse control signal controlling a number of laser pulses in each pulse picking cycle to be output from the surgical system; and wherein the operating range of the adjustable input device is configured to allow an operator to control dynamically the pulse control signal.

2. The surgical system as recited in claim 1, wherein the optical switching device is further configured to control an amount of energy of the laser pulses emitted from the laser that is output from the surgical system.

3. The surgical system as recited in claim 2, wherein the operating range of the adjustable input device is configured to allow an operator to control dynamically the amount of energy of the laser pulses emitted from the laser that is output from the surgical system.

4. The surgical system as recited in claim 3,
wherein the optical switching control signals communicated by the laser pulse controller to the optical switching device comprise a power level signal controlling the amount of energy of the laser pulses to be output from the surgical system; and
wherein the operating range of the adjustable input device is configured to allow an operator to control dynamically the power level signal.

5. The surgical system as recited in claim 2,
wherein in a first operating mode of the surgical system, the operating range of the adjustable input device is configured to allow an operator to control dynamically the amount of energy of the laser pulses emitted from the laser that is output from the surgical system; and
wherein in a second operating mode of the surgical system, the operating range of the adjustable input device is configured to allow an operator to control dynamically the percentage of laser pulses emitted from the laser that are output from the surgical system.

6. The surgical system as recited in claim 1, wherein the optical switching device comprises a shutter and a shutter motor.

7. The surgical system as recited in claim 6, wherein the shutter motor is configured to move the shutter in an alternating manner between a first position corresponding to the first condition of the optical switching device and a second position corresponding to the second condition of the optical switching device.

8. The surgical system as recited in claim 7, wherein the shutter comprises a mirror.

9. The surgical system as recited in claim 8, wherein the shutter motor comprises a galvanometer motor.

10. The surgical system as recited in claim 6, wherein the optical switching device further comprises a laser energy control system configured to regulate an amount of electromagnetic energy of each laser pulse that exits the surgical system.

11. The surgical system as recited in claim 10, wherein the laser energy control system comprises:
a waveplate;
a waveplate motor; and
a polarizer plate;
wherein the waveplate motor is configured to move the waveplate into different positions corresponding to different percentages of laser electromagnetic energy permitted to pass through the laser energy control system.

12. The surgical system as recited in claim 1, wherein the optical switching device comprises a pockels cell.

13. The surgical system as recited in claim 1, wherein the adjustable input device comprises a foot pedal configured to be actuated over the operating range.

14. A surgical system comprising:
a laser configured to emit electromagnetic radiation in laser pulses;
an optical switching device configured to switch between a first condition in which it allows laser pulses emitted from the laser to be output from the surgical system and a second condition in which it prevents laser pulses emitted from the laser from being output from the surgical system;
an adjustable input device configured to be actuated over an operating range; and
a laser pulse controller configured to communicate optical switching control signals to the optical switching device, wherein the optical switching control signals are based on input from the adjustable input device;
wherein the operating range of the adjustable input device is configured to allow an operator to control dynamically the laser pulses being output from the surgical system;
wherein the optical switching device comprises a shutter and a shutter motor;
wherein the shutter has an axis of rotation and at least one open area and at least one solid area arranged around the axis of rotation of the shutter;
wherein the shutter motor is configured to rotate the shutter around the axis of rotation of the shutter;
wherein the first condition of the optical switching device corresponds to a position of the shutter in which a solid area of the shutter is not in a path of the laser pulses emitted from the laser; and
wherein the second condition of the optical switching device corresponds to a position of the shutter in which a solid area of the shutter is in the path of the laser pulses emitted from the laser.

* * * * *